(12) United States Patent
Thurkauf et al.

(10) Patent No.: US 7,101,887 B2
(45) Date of Patent: *Sep. 5, 2006

(54) 1-PHENYL-4-BENZYLPIPERAZINES DOPAMINE RECEPTOR SUBTYPE SPECIFIC LIGANDS

(75) Inventors: Andrew Thurkauf, Danbury, CT (US); Xi Chen, Clinton, CT (US)

(73) Assignee: Neurogen Corporation, Branford, CT (US)

( * ) Notice: Subject to any disclaimer, the term of this patent is extended or adjusted under 35 U.S.C. 154(b) by 0 days.
This patent is subject to a terminal disclaimer.

(21) Appl. No.: 11/167,735

(22) Filed: Jun. 27, 2005

(65) Prior Publication Data
US 2005/0239799 A1    Oct. 27, 2005

Related U.S. Application Data

(63) Continuation of application No. 10/667,821, filed on Sep. 22, 2003, now abandoned, which is a continuation of application No. 10/186,235, filed on Jun. 28, 2002, now Pat. No. 6,656,943, which is a continuation of application No. 09/736,566, filed on Dec. 13, 2000, now Pat. No. 6,426,347, which is a continuation of application No. 09/228,106, filed on Jan. 11, 1999, now Pat. No. 6,172,229, which is a continuation of application No. 08/791,673, filed on Jan. 30, 1997, now Pat. No. 5,859,246.

(51) Int. Cl.
*A61K 31/495* (2006.01)
*C07D 295/076* (2006.01)

(52) U.S. Cl. .................. 514/255.03; 544/392
(58) Field of Classification Search ................ 544/392; 514/255.03
See application file for complete search history.

(56) References Cited

U.S. PATENT DOCUMENTS

| | | | |
|---|---|---|---|
| 3,299,067 A | | 1/1967 | Regnier et al. |
| 4,260,610 A | | 4/1981 | Regnier et al. |
| 5,607,946 A | | 3/1997 | Kulagowski et al. |
| 5,859,246 A | * | 1/1999 | Thurkauf et al. ........... 544/392 |
| 6,172,229 B1 | * | 1/2001 | Thurkauf et al. ........... 544/392 |
| 6,426,347 B1 | * | 7/2002 | Thurkauf et al. ...... 514/255.03 |
| 6,656,943 B1 | * | 12/2003 | Thurkauf et al. ...... 514/255.03 |

FOREIGN PATENT DOCUMENTS

| | | |
|---|---|---|
| EP | 574271 | 12/1993 |
| HU | 211 523 A9 | 6/1995 |
| WO | WO 93/04682 | 3/1993 |
| WO | WO 93/04684 | 3/1993 |
| WO | WO 94/06768 | 3/1994 |
| WO | WO 94/20471 | 9/1994 |
| WO | WO 97/41108 | 11/1997 |

OTHER PUBLICATIONS

Reitz et al. J. med. Chem. 37 (8), p. 1060-1062 (1994).*
Drug Evaluations by the American Medical Association, p. 380 (1983).*
Reitz, et al., J. Med. Chem. 37, 1060-1062, 1994.
Schmidt and Martin, (1965), Toxicol. Appl. Pharmacol., 7: pp. 257-267.
Meyers, et al.,(1964), J. Org. Chem., 29: pp. 1435-1438.
Sarati, S. et al., (1991), Psychopharmacology, "Kinetics of PIREBEDIL and effects on dopamine metabolisim: hepatic biotransformation is not a determinat of its dopaminergic action in rats" 105: pp. 541-545, XP002065935.
Boyfield, L. et al., (1996), Bioorg. & Med. Chem. Lett., "N-(Substituted-Phenyl)-Piperazines: Antagonists with high Binding and Functional Selectivity for Dopamine D4 Receptors" 6:(11), pp. 1227-1232.
Reitz, A.B. et al., (1995), J. Med. Chem., "N-Aryl-N'-Benzylpiperazines as Potential Antipsychotic Agents", 38:(21) pp. 4211-4215.
Handley, M.S., (1996), Medicinal Research Reviews, "D4 Receptors and Their Antagonists", 16:(6) pp. 507-526.
Mach, R.H. et al., (1993), Nucl. Med. Biol., "The use of '18F14-Fluorobenzyl Iodide (FB1) in PET Radiotracer Synthesis: Model Alkylation Studies and It's Application in the Design of Dopamine D1 and D2 Receptor-based Imaging Agents", 20:(6) pp. 777-794. XP002065565.
Prasad R. N. et al., (1968), Journal of Medicinal Chemistry, "Potential Antihypertensive Agents. II. Unsymmetrically 1,4-Disubstituted Piperazines. I" 11:(6) pp. 1144-1150. XP002036253.
Chemical Abstracts, vol. 59, No. 8732b, Morren et al.
J. Med. Chem. 1992, 35, 2369-2374, Mokrosz et al.
Morren, H. et al., "New Derivatives, N, N'-disubstituted for piperazine, with neurotropic properties", Industrie Chimique Beige-No. 2-1963, 123-134. (with translation).

* cited by examiner

*Primary Examiner*—Emily Bernhardt
(74) *Attorney, Agent, or Firm*—McDonnell Boehnen Hulbert & Berghoff LLP

(57) ABSTRACT

Disclosed are compounds of the formula:

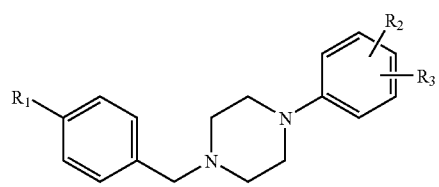

or the pharmaceutically acceptable addition salts thereof wherein:

$R_1$ is halogen or $C_1$–$C_4$ alkyl; and $R_2$ and $R_3$ are the same or different and represent hydrogen, halogen, $C_1$–$C_4$ alkyl, $C_1$–$C_4$ alkoxy, alkylthio, hydroxy, amino, mono($C_1$–$C_4$)alkylamino, di($C_1$–$C_4$) alkylamino, or $R_2$ and $R_3$ together represent a 4 carbon alkenylene moiety that together with the phenyl ring to which they are attached form a naphthyl moiety, which compounds are useful in the treatment of neuropsycological diseases such as schizophrenia, psychotic depression and mania.

13 Claims, No Drawings

1-PHENYL-4-BENZYLPIPERAZINES DOPAMINE RECEPTOR SUBTYPE SPECIFIC LIGANDS

BACKGROUND OF THE INVENTION

1. Field of the Invention

This invention relates to certain 1-phenyl-4-benzylpiperazines and pharmaceutical compositions containing them. It also relates to the use of such compounds in the treatment or prevention of psychotic disorders such as schizophrenia and other central nervous system diseases. The use of the compounds of this invention to the treatment of these disorders is indicated by the ability of the compounds to bind selectively to dopamine receptor subtypes.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of D2 receptors in the striatal region of the brain. The dopamine D4 receptor subtype has recently been identified (Van Tol, H. H. et al., Nature, 1991, 350, 610). Its unique localization in limbic brain areas and its differential recognition of various antipsychotics suggest that the D4 receptor play a role in the etiology of schizophrenia Selective D4 antagonists are effective antipsychotics free from the neurological side effects displayed by conventional neuroleptics.

Since dopamine D4 receptors are concentrated in the limbic system which controls cognition and emotion, compounds which interact with these receptors have utility in the treatment of cognitive disorders. Such disorders include the cognitive deficits which are a significant component of the negative symptoms (social withdrawal and unresponsiveness) of schizophrenia. Other disorders involving memory impairment or attention deficit disorders can also be treated with compounds that interact specifically with the dopamine D4 receptor subtype.

Japanese patent JP 47017306 discloses m-trifluoromethylphenyl benzyl piperazines as tranquilizers and analgetic agents. Nucl. Med. Biol. 20(6), 777–94, 1993, discloses radiolabelled 1-([4-{fluoro-18F}phenyl]methyl)-4-(3-[trifluoromiethyl]phenylpiperazine as an imaging agent.

J. Med. Chem. 37, 1060–1062, 1994, and International Application No. WO 9304684 discloses 4-arylpiperazines and 4-arylpiperidines.

J. Med. Chem. 11, 11441150, 1968, discloses certain 1-phenyl 4-benzyl piperazines as antiherpeusive agents.

SUMMARY OF THE INVENTION

This invention provides novel compounds of Formula I which interact with dopamine receptor subtypes. Accordingly, a broad embodiment of the invention is directed to a compound of Formula I:

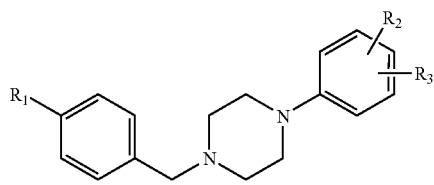

I or the pharmaceutically acceptable addition salts thereof wherein:

$R_1$ is halogen or $C_1$–$C_4$ alkyl; and $R_2$ and $R_3$ are the same or different and represent hydrogen, halogen, $C_1$–$C_4$ alkyl, $C_1$–$C_4$ alkoxy, alkylthio, hydroxy, amino, mono($C_1$–$C_4$)alkylamino, di($C_1$–$C_4$)alkylamino, or $R_2$ and $R_3$ together represent a 4 carbon alkenylene moiety that together with the phenyl ring to which they are attached form a naphthyl moiety.

The compounds of the present invention demonstrate high affinity and selectivity in binding to the Dopamine D4 receptor subtype. Consequently, they are useful in the treatment of schizophrenia, psychotic depression and mania. Other dopamine-mediated diseases such as Parkinsonism and tardive dyskinesias can also be treated directly or indirectly by modulation of D4 receptors. Compounds of the invention are also useful in treating the extrapyramidal side effects associated with the use of conventional neuroleptic agents as well as in the treatment of other disorders which respond to dopaminergic blockade such as substance abuse and obsessive compulsive disorder.

Furthermore, compounds of this invention are useful in treating depression, memory-impairment or Alzheimers disease by modulation of D4 receptors which selectively exist in limbic areas known to control emotion and cognitive functions. The interaction of 1-phenyl-4-benzylpiperazines with dopamine receptor subtypes is shown. This interaction results in the pharmacological activities of these compounds.

The invention further provides pharmaceutical compositions comprising compounds of Formula I. It also relates to the use of such compounds and compositions in the treatment and/or prevention of neuropsychological disorders including, but not limited to, schizophrenia, mania, dementia, depression, anxiety, dystonia, compulsive behavior, substance abuse, memory impairment, cognitive deficits, Parkinson-like motor disorders and motion disorders related to the use of neuroleptic agents.

DETAILED DESCRIPTION OF THE INVENTION

As mentioned above, the invention encompasses substituted 1-Phenyl-4-benzylpiperazines of formula I. Preferred compounds of formula I are those where $R_2$ and $R_3$ may not be 2-isopropoxyl and hydrogen, respectively, when $R_1$ is bromo.

The invention also encompasses compounds of formula II:

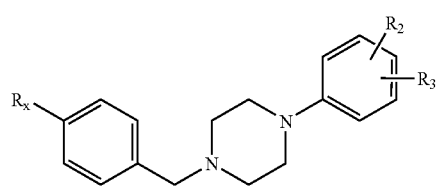

II wherein $R_x$ is fluorine, chlorine, bromine, or iodine; and $R_2$ and $R_3$ are the same or different and represent hydrogen, halogen, $C_1$–$C_4$ alkyl, $C_1$–$C_4$ alkoxy, alkylthio, hydroxy, amino, monoalkylamino or dialkylamino.

In preferred embodiments of formula II, $R_2$ and $R_3$ may not be 2-isopropoxyl and hydrogen, respectively, when $R_1$ is bromo. More preferred compounds of formula II are those where $R_x$ is chloride; $R_2$ and $R_3$ may not be 2-isopropoxyl and hydrogen, respectively, when $R_1$ is bromo; $R_2$ is halogen, most preferably chloride, or methyl or methoxy, and $R_3$ is hydrogen or methyl.

The invention also encompasses compounds of formula III:

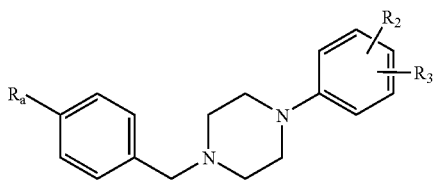

III wherein $R_x$ is $C_1$–$C_4$ alkyl; and $R_2$ and $R_3$ are the same or different and represent hydrogen, halogen, $C_1$–$C_4$ alkyl, $C_1$–$C_4$ alkoxy, alkylthio, hydroxy, amino, monoalkylamino or dialkylamino.

In preferred embodiments of formula III, $R_x$ is methyl; $R_2$ is halogen, most preferably chloride, or methyl or methoxy; and $R_3$ is hydrogen or methyl.

Particularly preferred compounds of formulas II and III are those where the phenyl group substituted with $R_2$ and/or $R_3$ is selected from the group consisting of:

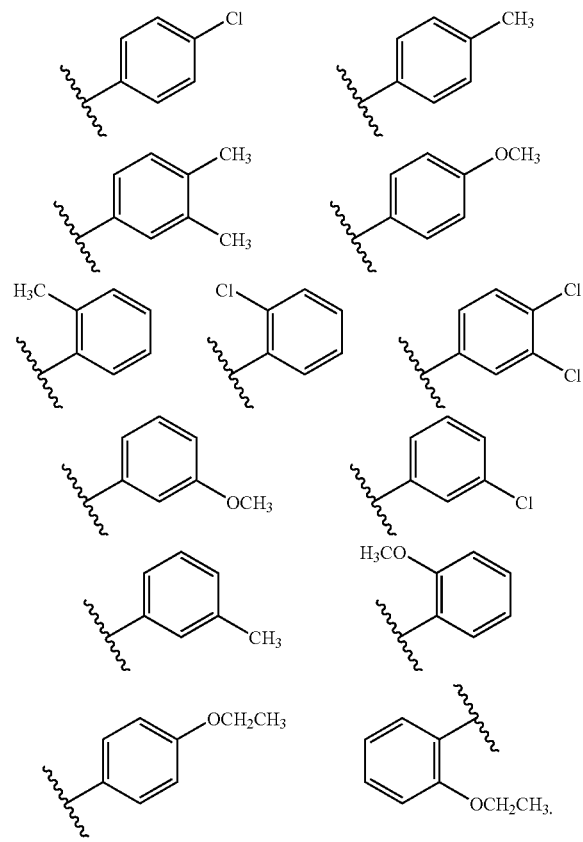

The invention also encompasses compounds of formula VI:

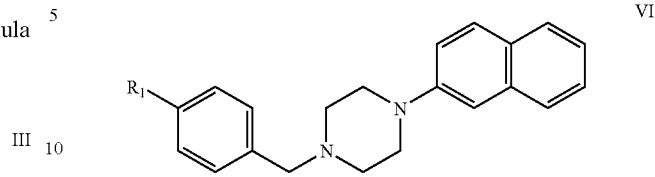

VI wherein $R_1$ is $C_1$–$C_4$ alkyl or halogen.

Preferred compounds of formula VI are those where $R_x$ is methyl, Cl, or F.

The invention also encompasses a method for treating or preventing neuropsychological disorders such as, for example, schizophrenia and other central nervous system diseases which comprises administering to a patient in need of such treatment a compound of the invention.

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromine, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By the terms $C_1$–$C_4$ alkyl and lower alkyl is meant straight and branched chain alkyl groups having from 1–4 carbon atoms as well as cyclic alkyl groups such as, for example, cyclopropyl and cyclobutyl. Specific examples of such alkyl groups are methyl, ethyl, propyl, isopropyl, n-butyl, isobutyl, tert-butyl, and sec-butyl. Preferred $C_1$–$C_4$ alkyl groups are ethyl and ethyl.

By the terms $C_1$–$C_4$ alkoxy and lower alkoxy is meant straight and branched chain alkoxy groups having from 1–4 carbon atoms.

By the term alkylthio is meant lower alkyl groups bound to the parent system, e.g., a phenyl group, by a sulfur atom.

By halogen, halo, or halide is meant fluorine, chlorine, bromine and iodine substituents.

Representative examples of compounds according to the invention are shown in Table 1 below.

TABLE 1

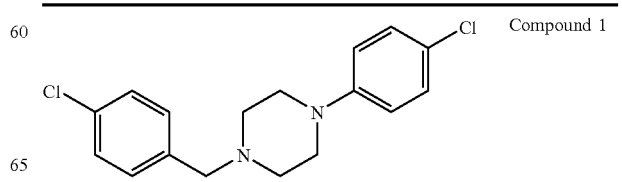

Compound 1

TABLE 1-continued

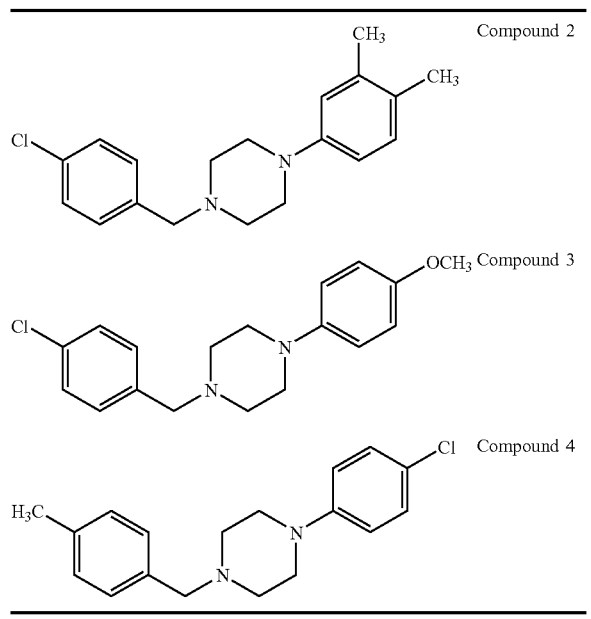

The pharmaceutical utility of compounds of this invention are indicated by the following assays for dopamine receptor subtype affinity.

Assay For D2 and D4 Receptor Binding Activity

Pellets of COS cells containing recombinantly produced D2 or D4 receptors from human are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described above and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM 3H-YM 09151-2 and the compound of interest in a total incubation mixture of 1.0 ml. Nonspecific binding is defined as that binding found in the presence of 1 mM spiperone; without further additions, nonspecific binding is less than 20% of total binding. Representative binding characteristics for compounds of the invention for the D2 and D4 receptor subtypes are shown in Table 2 for cloned human dopamine receptors. Typically, the compounds of the invention have similar binding profiles.

TABLE 2

| Compound Number | D4 Ki (nM) | D2 Ki (nM) |
|---|---|---|
| 1 | 5 | >1000 |
| 2 | 16 | >600 |
| 3 | 5 | >1000 |
| 4 | 15 | >300 |

Compound numbers relate to compounds described below in the examples.

The compounds disclosed in Japanese patent JP 47017306 and *Nucl. Med. Biol.* 20(6), 777–94, 1993 were prepared and tested using the above assay. Those compounds did not selectively bind to dopamine subtypes.

The compound disclosed in *J. Med. Chem.* 11, 1144–1150, 1968, as Compound 97, i.e., a 4-methoxy derivative, was prepared and found to not selectively bind to dopamine subtypes.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturallyoccurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitot monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative illustration of methods suitable for the preparation of compounds of the present invention is shown in Schemes I. Those having skill in the art will recognize that the starting materials may be varied and additional steps employed to produce compounds encompassed by the present invention. For example, in certain situations, protection of reactive moieties such as amino groups, will be required.

Preparation of 1-Phenyl-4-Benzylpiperazines

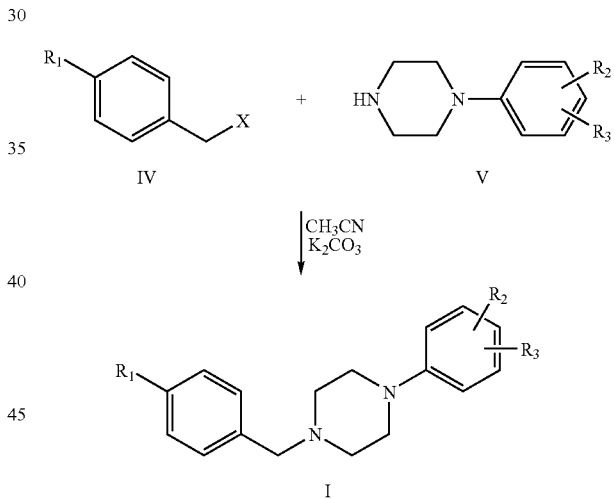

In the above scheme, $R_1$, $R_2$ and $R_3$ are as defined above for formula I.

As shown, a 4-substituted benzyl alkylating agent of general Structure IV, possessing an appropriate leaving group X, is reacted with a 1-phenylpiperazine of general structure V in the presence of a suitable base to afford a compound of Formula I as the desired product. The leaving group X may be a halogen, a sulfonic acid ester or the like. The reaction is typically carried out in a solvent such as acetonitrile with heating at, for example, reflux.

Where they are not commercially available, the compounds of general structures IV and V may be prepared using known procedures or procedures analogous to those described in literature. Those having skill in the art will recognize that the starting materials may be varied and additional steps employed to produce compounds encompassed by the present invention.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

1-(4-chlorophenyl)-4-(4-chlorobenzyl)piperazine dihydrochloride (Compound I)

A mixture of 1-(4-chlorophenyl)piperazine (1.61 g, 0.01 mole), 4-chlorobenzyl chloride (2.10 g, 0.01 mole) and potassium carbonate (2 g) in acetonitrile (40 mL) is heated at reflux for 6 hours under a nitrogen atmosphere. After cooling, the reaction mixture is poured into water (50 mL) and ether (50 mL). The aqueous layer is discarded and the organic layer is extracted with 1 N aqueous hydrochloric acid solution. The acidic extract is neutralized with 6 N ammonium hydoxide solution and extracted with ether. The organic layer is dried ($Na_2SO_4$) and concentrated to provide the crude free base of the desired unsymmetrically substituted piperazine. This material is dissolved in warm isopropanol (10 mL) and treated with a 1 N solution of HCl in ether until acidic to pH paper. Upon cooling, crystals of dihydrochloride salt are collected (2.2 g, 56%).

The following compounds are prepared essentially according to procedures set forth above in Example 1.

(a) 1-(3-chlorophenyl)-4-(chlorobenzyl)piperazine dihydrobromide (m.p. 238–240° C.)
(b) 1-(2-chlorophenyl)-4-(4-chlorobenzyl)piperazine dioxalate (m.p. 203–204° C.)
(c) 1-(3,4-dichlorophenyl)-4-(chlorobenzyl)piperaine (m.p. 82–83° C.)
(d) 1-(4-methylphenyl)-4-(chlorobenzyl)piperazine dioxalate (m.p. 204–206° C.)
(e) 1-(3-methylphenyl)-4-(chlorobenzyl)piperazine dioxalate (m.p. 233–235° C.)
(f) 1-(2-methylphenyl)-4-(chlorobenzyl)piperazine dioxalate (m.p. 205–206° C.)
(g) 1-(3,4-diethylphenyl)-4-(4-chlorobenzyl)piperazine dihydrochloride. (m.p. 225–228° C., Compound 2)
(h) 1-(4-methoxyphenyl)-4-(4-chlorobenzyl)piperazine dioxalate (m.p. 211–212° C., Compound 3)
(i) 1-(3-methoxyphenyl)-4-(4-chlorobenzyl)piperazine dioxalate (m.p. 205–207° C.)
(j) 1-(2-methoxyphenyl)-4-(4-chlorobenzyl)piperazine dioxalate (m.p 217–220° C.)
(k) 1-(4-ethoxyphenyl)-4-(4-chlorobenzyl)piperazine dihydrochloride (m.p. 235–237° C.)
(l) 1-(2-ethoxyphenyl)-4-(4-chlorobenzyl)piperazine dihydrobromide (m.p. 215–217° C.)
(m) 1-phenyl-4-(4-chlorobenzyl)piperazine dioxalate (m.p. 228–231° C.)
(n) 1-(4-chlorophenyl)-4-(4-fluorobenzyl)piperazine dihydrobromide
(o) 1-(4-chlorophenyl)-4-(4-methylbenzyl)piperazine dihydrobromide (Compound 4)
(p) 1-(3-chlorophenyl)-4-(4-methylbenzyl)piperazine dioxalate (m.p. 199–200° C.)
(q) 1-(4-chlorophenyl)-4-(4-methylbenzyl)piperazine dioxalate (m.p. 219–221° C.)
(r) 1-(3,4-dichlorophenyl)-4-(4-methylbenzyl)piperazine dihydrobromide
(s) 1-(4-methylphenyl)-4-(4-methylbenzyl)piperazine dioxalate (m.p. 203–204° C.)
(t) 1-(2-methylphenyl)-4-(4-methylbenzyl)piperazine dioxalate (m.p. 180–182° C.)
(u) -methoxyphenyl)-4-(4-methylbenzyl)piperazine dihydrobromide
(v) -methoxyphenyl)-4-(4-methylbenzyl)piperazine dihydrobromide (m.p. 234–235° C.)

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A composition comprising a compound of the formula:

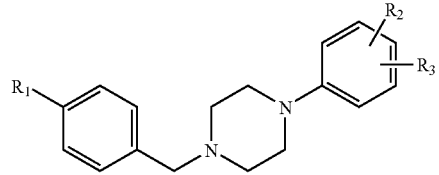

or a pharmaceutically acceptable acid salt thereof, and a pharmaceutically acceptable excipient, wherein:
$R_1$ is halogen or $C_1$–$C_4$ alkyl;
$R_2$ represents halogen, $C_1$–$C_4$ alkyl, $C_1$–$C_4$ alkoxy, $C_1$–$C_4$ alkylthio, hydroxy, amino, mono $C_1$–$C_4$ alkylamino or di $C_1$–$C_4$ alkylamino,
$R_3$ represesents hydrogen, halogen, $C_1$–$C_4$ alkyl, $C_1$–$C_4$ alkoxy, $C_1$–$C_4$ alkylthio, hydroxy, amino, mono $C_1$–$C_4$ alkylamino or di $C_1$–$C_4$ alkylamino,
with the proviso that $R_2$ and $R_3$ may not be 2-isopropoxyl and hydrogen respectively when $R_1$ is bromo.

2. A composition according to claim 1, wherein $R_1$ is methyl.

3. A composition comprising a compound of the formula:

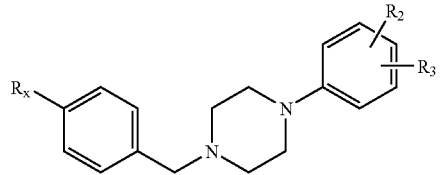

or a pharmaceutically acceptable salt thereof, and a pharmaceutically acceptable excipient, wherein
$R_x$ is fluorine, chlorine, bromine, or iodine; and
$R_2$ and $R_3$ are the same or different and represent hydrogen, halogen, $C_1$–$C_4$ alkyl, $C_1$–$C_4$ alkoxy, $C_1$–$C_4$ alkylthio, hydroxy, amino, mono $C_1$–$C_4$ alkylamino or di $C_1$–$C_4$ alkylanino;
with the proviso that $R_2$ and $R_3$ may not be 2-isopropoxyl and hydrogen, respectively, when $R_x$ is bromo.

4. A composition according to claim 3, wherein $R_x$ is chloride; $R_2$ is chloride, methyl, ethoxy or methoxy; and $R_3$ is chloride, hydrogen or methyl.

5. A composition according to claim 4, wherein the phenyl group substituted with $R_2$ and $R_3$ is selected from the group consisting of:

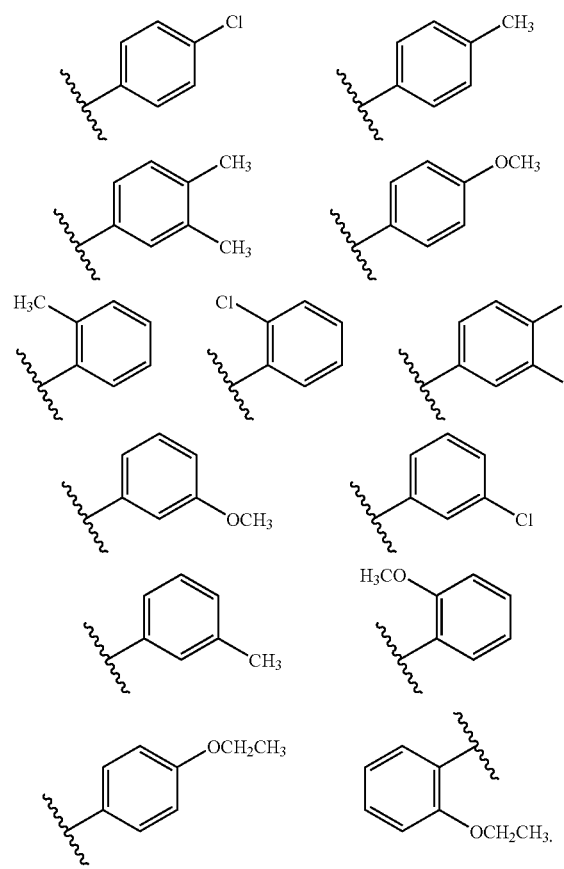

6. A composition comprising a compound of the formula:

9. A composition according to claim 7, wherein the phenyl group substituted with $R_2$ and $R_3$ is selected from the group consisting of:

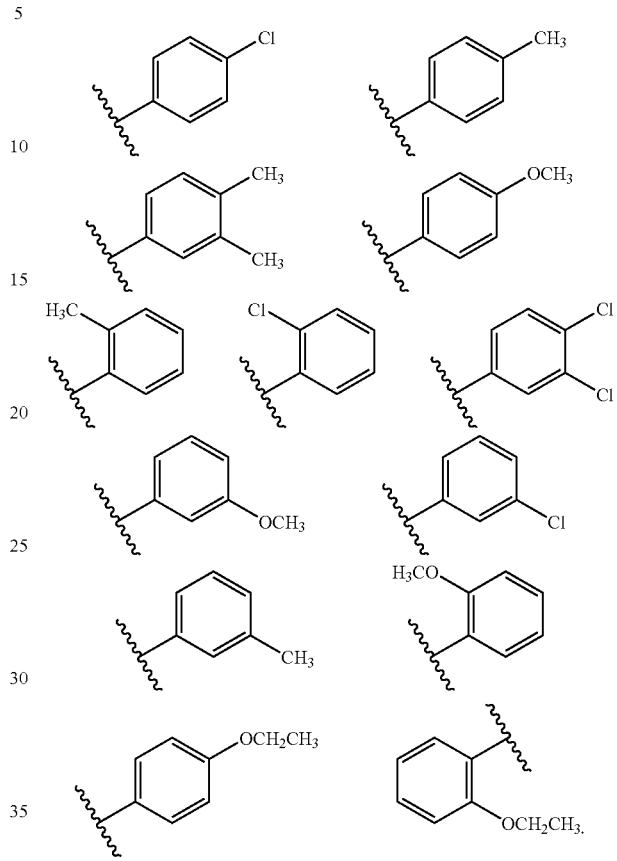

10. A composition comprising a compound of the formula:

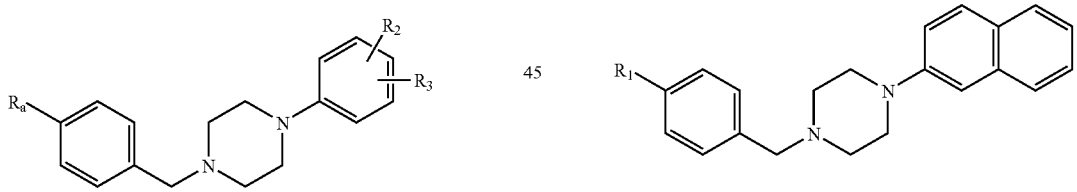

or a pharmaceutically acceptable salt thereof, and a pharmaceutically acceptable excipient, wherein $R_a$ is $C_1$–$C_4$ alkyl; and $R_2$ represents halogen, $C_1$–$C_4$ alkyl, $C_1$–$C_4$ alkoxy, $C_1$–$C_4$ alkylthio, hydroxy, amino, mono $C_1$–$C_4$ alkylamino or di $C_1$–$C_4$ alkylamino;

$R_3$ represents hydrogen, halogen, $C_1$–$C_4$ alkyl, $C_1$–$C_4$ alkoxy, $C_1$–$C_4$ alkylthio, hydroxy, amino, mono $C_1$–$C_4$ alkylamino or di $C_1$–$C_4$ alkylamino.

7. A composition according to claim 6, wherein $R_a$ is methyl.

8. A composition according to claim 6, wherein $R_2$ is chloride, fluoride, methyl or methoxy; and $R_3$ is hydrogen or methyl.

or a pharmaceutically acceptable salt thereof, and a pharmaceutically acceptable excipient, wherein:

$R_1$ is $C_1$–$C_4$ alkyl or halogen.

11. A composition according to claim 10, wherein $R_1$ is chloro.

12. A composition according to claim 1, wherein the compound is selected from the group consisting of:
 1-(3-chlorophenyl)-4-(4-chlorobenzyl)piperazine;
 1-(2-chlorophenyi)-4-(4-chlorobenzyl)piperazine;
 1-(3,4-dichiorophenyl)-4-(4-chlorobenzyl)piperazine;
 1-(4-methylphenyl)-4-(4-chlorobenzyl)piperazine;
 1-(3-methylphenyl)-4-(4-chlorobenzyl)piperazine;
 1-(2-methylphenyl)-4-(4-chlorobenzyl)piperazine;
 1-(3,4-dimethylphenyl)-4-(4-chlorobenzyl)piperazine;
 1-(4-methoxyphenyl)-4-(4-chlorobenzyl)piperazine;
 1-(3-methoxyphenyl)-4-(4-chlorobenzyl)piperazine;
 1-(2-methoxyphenyl)-4-(4-chlorobenzyl)piperazine;

1-(4-ethoxyphenyl)-4-(4-chlorobenzyl)piperazine;
1-(2-ethoxyphenyl)-4-(4-chlorobenzyl)piperazine;
1-(4chlorophenyl)-4-(4-fluorobenzyl)piperazine;
1-(4-chlorophenyl)-4-(4-methylbenzyl)piperazine;
1-(3-chlorophenyl)-4-(4-methylbenzyl)piperazine;
1-(3,4-dichioropheryl)-4-(4-methylbenzyl)piperazine;
1-(4-methylphenyl)-4-(4-methylbenzyl)piperazine;
1-(2-methylphenyl)-4-(4-methylbenzyl)piperazine;
1-(4-methoxyphenyl)-4-(4-methylbenzyl)piperazine;
1-(2-methoxyphenyl)-4-(4-methylbenzyl)piperazine;
1-(4-chlorophenyl)-4-(4-chlorobenzyl)piperazine; and
pharmaceutically acceptable salts thereof.

13. A composition according to claim 3 wherein the compound is 1-phenyl-4-(4-chlorobenzyl)piperazine, or a pharmaceutically acceptable salt thereof.

* * * * *